(12) United States Patent
Lewis

(10) Patent No.: US 7,217,512 B2
(45) Date of Patent: May 15, 2007

(54) REAGENT AND METHOD FOR ATTACHING TARGET MOLECULES TO A SURFACE

(75) Inventor: Mark A. Lewis, Corning, NY (US)

(73) Assignee: Corning Incorporated, Corning, NY (US)

( * ) Notice: Subject to any disclaimer, the term of this patent is extended or adjusted under 35 U.S.C. 154(b) by 665 days.

(21) Appl. No.: 10/143,439

(22) Filed: May 9, 2002

(65) Prior Publication Data

US 2003/0215806 A1 Nov. 20, 2003

(51) Int. Cl.
*C12Q 1/68* (2006.01)
*C07H 21/00* (2006.01)

(52) U.S. Cl. .............................. 435/6; 435/5; 536/23.1; 536/25.3

(58) Field of Classification Search .................... 435/5, 435/6; 536/23.1, 25.3
See application file for complete search history.

(56) References Cited

U.S. PATENT DOCUMENTS

| | | | |
|---|---|---|---|
| 4,141,857 A | 2/1979 | Levy et al. | 252/430 |
| 4,529,618 A | 7/1985 | Ponjee et al. | 427/82 |
| 4,581,336 A | 4/1986 | Malloy et al. | 435/176 |
| 5,087,522 A | 2/1992 | Bailly et al. | 428/402 |
| 5,474,796 A | 12/1995 | Brennan | 427/2.13 |
| 5,510,270 A | 4/1996 | Fodor et al. | 436/518 |
| 5,688,642 A * | 11/1997 | Chrisey et al. | 435/6 |
| 5,728,588 A | 3/1998 | Caldwell | 436/532 |
| 5,858,653 A | 1/1999 | Duran et al. | 435/6 |
| 5,959,098 A | 9/1999 | Goldberg et al. | 536/25.3 |
| 6,159,695 A | 12/2000 | McGovern et al. | 435/6 |
| 6,475,945 B1 * | 11/2002 | Carnahan et al. | 502/87 |
| 6,548,264 B1 | 4/2003 | Tan et al. | 435/7.21 |
| 6,750,023 B2 | 6/2004 | Tanner et al. | 435/6 |
| 6,943,133 B2 * | 9/2005 | Vogel | 502/104 |
| 2003/0054176 A1 | 3/2003 | Pantano et al. | 428/429 |
| 2003/0059819 A1 | 3/2003 | Tzeng et al. | 435/6 |
| 2003/0099930 A1 | 5/2003 | Graves et al. | 435/5 |
| 2004/0043508 A1 | 3/2004 | Frutos et al. | 436/518 |
| 2004/0076961 A1 | 4/2004 | Lewis | 435/6 |
| 2004/0086939 A1 | 5/2004 | Hancock et al. | 435/7.1 |
| 2004/0146460 A1 | 7/2004 | Satafsky | |

FOREIGN PATENT DOCUMENTS

| | | |
|---|---|---|
| WO | WO99/57323 | 11/1999 |
| WO | WO03/083477 | 10/2003 |

OTHER PUBLICATIONS

Kazuyuki Hayashi et al., "Regulation of the Surface Potential of Silicon Substrates in Micrometer Scale with Organosilane Self-Assembled Monolayers", Langmuir 2002, vol. 18, pp. 7469-7472.
Soon Jin Oh et al., "Characteristics of DNA Microarrays Fabricated on Various Aminosilane Layers", Langmuir 2002, vol. 18, pp. 764-1769.
Advanced Organic Chemistry; Reactions, Mechanisms and Structure, Wiley, New York 1992, p. 1016.
U.S. Appl. No. 11/027,318, filed Dec. 30, 2004, Mark A. Lewis.
Linda A. Chrisey, Gil U. Lee, C. Elizabeth O'Ferrall, "Covalent Attachment of Synthetic DNA to Self-Assembled Movolayer Films," Nucleic Acids Research, 1996, vol. 24, No. 15, 3031-3039.

* cited by examiner

*Primary Examiner*—Jezia Riley
(74) *Attorney, Agent, or Firm*—Lawrence A. Villanueva, Esq.; Thomas R. Beall

(57) ABSTRACT

The present invention provides a method and reagent composition for attachment of target molecules onto the surface of a substrate, such as microwell plates, tubes, beads, microscope slides, silicon wafers or membranes. In one embodiment, the method and composition are used to immobilize nucleic acid probes onto plastic materials such as microwell plates, e.g., for use in hybridization assays. In a preferred embodiment, the method and composition are adapted for use with substantially flat surfaces, such as those provided by microscope slides and other plastic, silicon hydride, or organosilane-pretreated glass or silicone slide support surfaces. The reagent composition can then be used to attach a target molecule such as a biomolecule (e.g., a nucleic acid) which in turn can be used for specific binding reactions (e.g., to hybridize a nucleic acid to its complementary strand).

26 Claims, 5 Drawing Sheets

Slide #149

Printed DNA (65/65)

Slide #150

Printed DNA (65/65)

Slide #149

Following prehyb/boil (65/65)

Slide #150

Following prehyb/boil (65/65)

Slide #149

Hyb channel 2 (95/95)

Slide #150

Hyb channel 2 (95/95)

Slide #149

Hyb channel 1 (95/95)

Slide #150

Hyb channel 1 (95/95)

Slide #483 new slide – no BSA
Freshly printed DNA (65/65)

Slide #483 new slide – no BSA
After prehyb and boil (65/65)

Slide #482 new slide – with BSA
Freshly printed DNA (65/65)

Slide #482 new slide – with BSA
After prehyb and boil (65/65)

Slide #387 – old slide
Freshly printed DNA (65/65)

Slide #387 – old slide
After prehyb and boil (65/65)

Slide #387 – old slide
Hyb channel 2 (65/65)

Slide #387 – old slide
Hyb channel 1 (85/85)

Slide #482 new slide – with BSA
Hyb channel 2 (65/65)

Slide #482 new slide – with BSA
Hyb channel 1 (85/85)

Slide #483 new slide – no BSA
Hyb channel 2 (65/65)

Slide #483 new slide – no BSA
Hyb channel 1 (85/85)

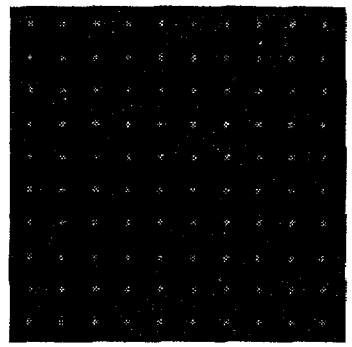
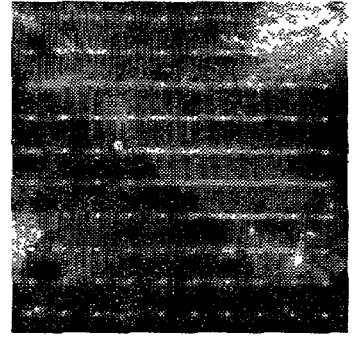
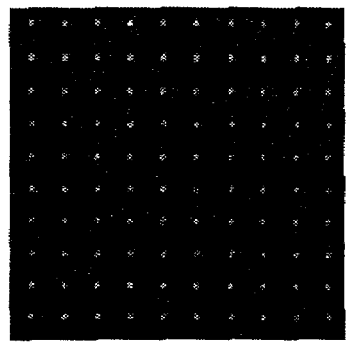
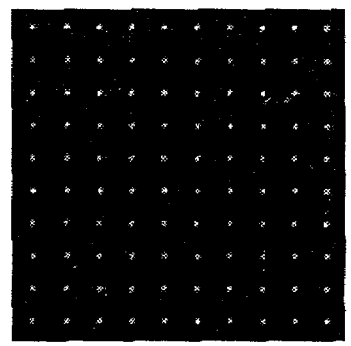
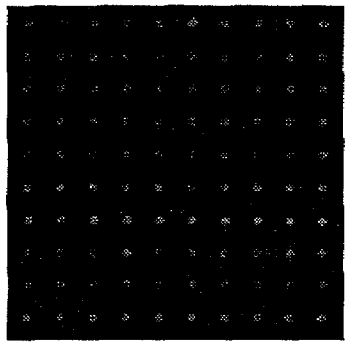
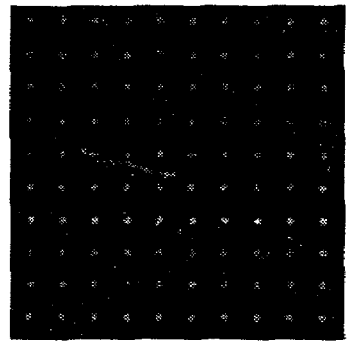

REAGENT AND METHOD FOR ATTACHING TARGET MOLECULES TO A SURFACE

BACKGROUND OF THE INVENTION

1. Field of the Invention

The present invention relates generally to reagents and methods for attaching target molecules such as oligonucleotides (oligos) to a surface. The present invention further relates to the resultant coated surfaces themselves.

2. Technical Background

A biological array can contain a chosen collection of biomolecules, for example, probes specific for important pathogens, sequence markers, antibodies, immunoglobulins, receptor proteins, peptides, cells, and the like. For example, an array can contain a chosen collection of oligonucleotides specific for known sequence markers of genetic diseases or probes to isolate a desired protein from a biological sample. A biological array may comprise a number of individual biomolecules tethered to the surface of a substrate in a regular pattern, each one in a different area, so that the location of the biomolecule is known.

Biomolecule arrays can be synthesized directly on a substrate employing methods of solid-phase chemical synthesis in combination with site-directing mass as disclosed in U.S. Pat. No. 5,510,270, incorporated herein by reference; photolithographic techniques involving precise drop deposition using piezoelectric pumps, as disclosed in U.S. Pat. No. 5,474,796, incorporated herein by reference; or contacting a substrate with typographic pins holding droplets and using ink jet printing mechanisms to lay down an array matrix.

Commercially available substrates for heterogeneous assays capable of immobilization of biomolecules such as SuperAldehyde™ from CloneTech or 3D link™ slides from Surmodics' do not have appropriate capability for covalent attachment of biomolecules, e.g., smaller oligonucleotides of less than 500 nucleotides. The SuperAldehyde™ slide requires an additional reduction step to stabilize a covalent attachment between the slide and the biomolecule. This causes problems in some heterogeneous assays as the fluorescent signal from a label on the biomolecule may be reduced or damaged. The Surmodics' slides on the other hand require gentle contact or ink jet printing.

There are those who believe that the covalent attachment of the target to the surface allows for a better product. They further believe that generating the probe on the surface using methods of solid phase synthesis is a better process than attaching the final product to a modified surface. While this might avoid the complications of adding an anchor point (functionality added for the specific purpose of surface reaction) it produces the unavoidable consequence of any linear non-convergent synthesis which results in a low yield of the desired product. For example, a 10 step linear synthesis giving a 95% yield in each step gives a final yield of only 60%. The synthesis of a 20-mer gives a final yield of 36% and a 30-mer gives final yield of 21%. By the time a 50-mer is reached only 8% is the desired product left. The other 92% are fragments left over during each synthesis step. An added complication is that each fragment may react in any subsequent synthetic step, which in turn generates any number of alternate sequences than the desired one. This has the ultimate problem of producing false positives during the hybridization reaction. It would be ideal if each synthesis reaction could produce the 95% yield which is not realistic since each step suffers some loss attributed to several factors which include, but are not limited to, bad reagents, wrong time and/or temperature, and contamination.

The case of the aldehyde surface that attaches to a primary amine to form the imine (Schiff Base) requires the use of a hydride reducing agent to stabilize the bond. The reason the bond is unstable is that imines are susceptible to hydrolysis giving back the amine and the aldehyde. Traditionally the hydride reducing agent is a borohydride in a less reactive form like the cyanoborohydride. The purpose of the cyano group is to reduce the reactivity of the protons which immediately forms $H_2$ in the presence of water and consumes the reagent. A problem with using boron is that it forms stable complexes with amine functions that usually need rigorous conditions to break. Another problem with these reducing agents is that they react with many carbonyl groups of which an aldehyde is merely one example. Amides are another type of carbonyl group present in the bases thymine, cytosine and guanine which can also be attacked by hydride reagents.

The use of a non-covalent interaction as the primary means of attachment has been accomplished by generating a positively charged surface, which then interacts with the intrinsic negative charge of the phosphate backbone of DNA. Primary amines are those which are protonated in neutral water (buffered pH ~7) and those that have a pKa of ~10, have been shown to work well. Primary amines used as a means of attachment include, but are not limited to, polylysines, GAPS, dendrimers. These primary amines also generate single point charge when protonated. Hard/Soft Acid Base (HSAB) Theory concludes that the interaction of like species gives stronger interactions than unlike species. For example, common counter ions for the ammonium cation ($NH_4^+$) is a chloride ($Cl^-$) hydroxide ($HO^-$). These are all ions that have no capability to resonate/delocalize the charge. The phosphate group, found in the backbone of DNA, has a negative charge that can be delocalized through resonance and thereby make it a softer charge. Ideally then a softer charged surface should interact more favorably (stronger) than a surface with point charges. Therefore, it would be highly desirable to have a method and reagent composition for the attachment of target molecules onto a surface of a substrate that can eliminate the specific binding problems associated with covalent attachments between the substrate and biomolecule.

SUMMARY OF THE INVENTION

The present invention provides a method and reagent composition for attachment of target molecules onto the surface of a substrate, such as microwell plates, tubes, beads, microscope slides, silicon wafers or membranes. In one embodiment, the method and composition are used to immobilize nucleic acid probes onto plastic materials such as microwell plates, e.g., for use in hybridization assays. In a preferred embodiment, the method and composition are adapted for use with substantially flat surfaces, such as those provided by microscope slides and other plastic, silicon hydride, or organosilane-pretreated glass or silicone slide support surfaces. The reagent composition can then be used to attach a target molecule such as a biomolecule (e.g., a nucleic acid) which in turn can be used for specific binding reactions (e.g., to hybridize a nucleic acid to its complementary strand).

Support substrates can be prepared from a variety of materials, including but not limited to plastic materials selected from the group consisting of crystalline thermoplastics (e.g., high and low density polyethylenes, polypropylenes, acetal resins, nylons and thermoplastic polyesters) and amorphous thermoplastics (e.g., polycarbonates and poly(methyl methacrylates). Suitable plastic or glass materials provide a desired combination of such properties as rigidity, toughness, resistance to long term deformation, recovery from deformation on release of stress, and resistance to thermal degradation.

A reagent composition of the invention for attaching a target molecule (e.g., nucleic acid) to the surface of a substrate contains functional groups of the

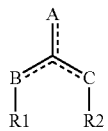

general formula (I):

In the formula, ----- represents a single or double bond forming a saturated or unsaturated portion of said functional group, provided that only one is unsaturated at a given time; a is N or H; b is S, N, C or O; c is N; and $R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other or part of a conjugated ring system; and c is protonated at acidic pH.

In one embodiment, the functional group of general formula (I) has an atom with a cationic charge conjugated to an atom with a lone pair of electrons. In a preferred embodiment, the functional group of general formula (I) is a guanidino, pyridyl or thiouronium group. In a more preferred embodiment, the functional group of general formula (I) is selected from the group:

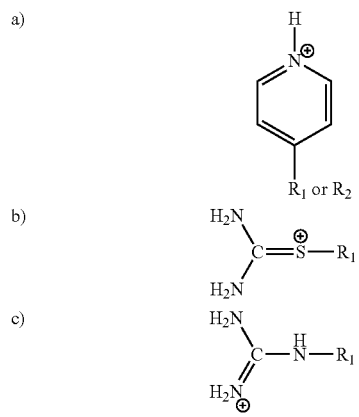

Preferably, the functional groups of general formula (I) form a cationic polymer and target molecules interact with the molecule of cationic polymer by hydrogen bonding and ionic interactions. More preferably, the phosphate group on the nucleic acid target molecule interacts with the functional group by hydrogen bonding and ionic interactions.

In another embodiment, the present invention provides a method for attaching target molecules, such as an oligo on the surface of a substrate, by employing a reagent as described herein. Generally, the reagent molecules will first be coated onto the surface of the substrate to form a surface bound polymer. Thereafter the target molecule, (e.g., an oligonucleotide) is contacted with the reagent under conditions suitable to permit it to come into binding proximity with the bound polymer. The target molecule interacts with the bound reagent by hydrogen bonding and ionic interaction between the reactive groups of the bound reagent and the phosphate group of the nucleic acid.

Additionally, the invention provides a surface having nucleic acids attached thereto by means of a reagent as described herein, as well as a material (e.g., microwell plate or slide) that provides such a surface.

Target molecules include, but are not limited to, plasmid DNA, cosmid DNA, bacteriophage DNA, genomic DNA (includes, but not limited to yeast, viral, bacterial, mammalian, insect), RNA, cDNA, PNA, and oligonucleotides.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed.

BRIEF DESCRIPTION OF THE FIGURES

FIGS. 3A–3L show false color images from three slides coated with thiouronium.

DETAILED DESCRIPTION OF THE INVENTION

Figure 1A:
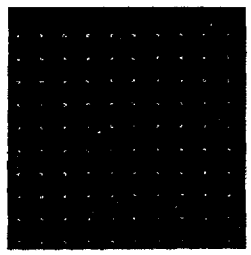
FIGS. 1A–1H show false color images from two slides coated with pyridinium.

A preferred reagent molecule of the present invention comprises a reagent composition of the invention for attaching a target molecule (e.g., nucleic acid) to the surface of a substrate contains functional groups of the general formula (I):

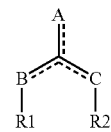

In the formula, ----- represents a single or double bond forming a saturated or unsaturated portion of said functional group, provided that only one is unsaturated at a given time; a is N or H; b is S, N, C or O; c is N; and $R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other or part of a conjugated ring system; and c is protonated at acidic pH.

In one embodiment, the functional group of general formula (I) has an atom with a cationic charge conjugated to an atom with a lone pair of electrons. In a preferred embodiment, the functional group of general formula (I) is a guanidino, pyridyl or thiouronium group. In a more preferred embodiment, the functional group of general formula (I) is selected from the group:

a) 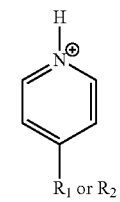

b) 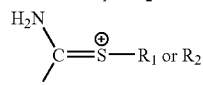

c) 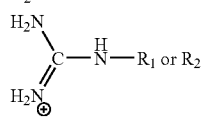

Preferably, the functional groups of general formula (I) form a cationic polymer and target molecules interact with the molecule of cationic polymer by hydrogen bonding and ionic interactions. More preferably, the phosphate group on the nucleic acid target molecule interacts with the functional group by hydrogen bonding and ionic interactions.

When used for preparing microarrays, e.g., to attach capture molecules. also referred to as target molecules, (e.g., oligonucleotides or cDNA) to the microarray surface, such capture molecules are generally delivered to the surface in a volume of less than about 1 nanoliter per spot, using printing pins adapted to form the spots into arrays having center to center spacing of about 200 µm to about 500 µm.

Given their small volumes, the printed target arrays tend to dry quickly, thus further affecting the coupling kinetics and efficiency. Unlike the coupling of DNA from solution and onto the surface of coated microplate wells, oligonucleotides printed in arrays of extremely small spot sizes tend to dry quickly, thereby altering the parameters affecting the manner in which the oligonucleotides contact and couple with the support. In addition to the design and handling of the printing pins, other factors can also affect the spot size, and in turn, the ultimate hybridization signals, including: salt concentrations, type of salts and wetting agents in the printing buffer, hydrophobic/hydrophilic properties of the surfaces; the size and/or concentration of the oligonucleotide; and the drying environments.

In a preferred embodiment, the reagent composition can be used to prepare coated slides having the reagent composition immobilized thereon. The slides can be stably stored and used at a later date to prepare microarrays.

Coated slides of the present invention are particularly well suited to replace conventional (e.g., silylated) glass slides in the preparation of microarrays using manufacturing and processing protocols, reagents and equipment such as microspotting robots (e.g., as available from Cartesian), and a chipmaker micro-spotting device (e.g., as available from TeleChem International). Suitable spotting equipment and protocols are commercially available, such as the "ArrayIt,"™ ChipMaker 3 spotting device.

The use of such an instrument, in combination with conventional (e.g., poly-1-lysine coated) slides, is well known in the art. See, for instance, U.S. Pat. No. 5,087,522 (Brown et al.) "Methods for Fabricating Microarrays of Biological Samples", and the references cited therein, the disclosures of each of which are incorporated herein by reference.

For instance, the method and system of the present invention can be used to provide a substrate, such as a glass slide, with a surface having one or more microarrays. Each microarray preferably provides at least about $100/cm^2$ (and preferably at least about $1000/cm^2$) distinct target molecules (e.g., polynucleotide or polypeptide biopolymers) in a surface area of less than about 1 $cm^2$. Each distinct target molecule 1) is disposed at a separate, defined position in the array, 2) has a length of at least 10 subunits, 3) is present in a defined amount between about 0.1 femtomoles and about 10 nanomoles, and 4) is deposited in selected volume in the volume range of about 0.01 nanoliters to about 100 nanoliters. These regions (e.g., discrete spots) within the array can be generally circular in shape, with a typical diameter of between about 10 microns and about 500 microns (and preferably between about 20 and about 200 microns). The regions are also preferably separated from other regions in the array by about the same distance (e.g., center to center spacing of about 20 microns to about 1000 microns).

Those skilled in the art, given the present description, will be able to identify and select suitable reagents depending on the type of target molecule of interest. Target molecules include, but are not limited to, plasmid DNA, cosmid DNA, bacteriophage DNA, genomic DNA (includes, but not limited to yeast, viral, bacterial, mammalian, insect), RNA, cDNA, PNA, and oligonucleotides.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments.

EXAMPLES

The invention will be further clarified by the following examples which are intended to be exemplary of the invention.

Example 1

All slides received the pre-treatment. The moisture sensitive procedure applies only to the silanes. The polyarginine was applied to the surface using the aqueous procedure.

Pre-Treatment

All the slides were subjected to a pre-treatment prior to surface modification with the trialkoxysilane. Because the slides have a non-uniform distribution of surface hydroxyls as well as possible organic contaminants, the slides were put in a staining dish that contained 4N NaOH and were stirred for 1 hour at room temperature. The slides were then removed from the hydroxide solution and dipped into a beaker containing DI water. The slide was agitated for a few seconds then rinsed with methanol. This process was repeated twice. Once all the slides had been washed and rinsed and placed into a clean staining dish, they were put into the oven (100° C. until needed). Just prior to surface modification, the slides were removed from the oven and cooled. The slides were then O2 plasma treated for 5 minutes at 200 Watts.

Moisture Sensitive Procedure

Since the alkoxysilane hydrolysis takes place in the presence of air, all the surface chemistry was done in a Dry Box (moisture free). The reagents were pumped into the dry box using 3 cycles of pump and back filling with 99.9999% Ar. The glassware needed for a surface chemistry reaction was taken directly from the oven and placed into the anti-chamber. Once all the glassware (including the pre-cleaned slides) were put into the anti-chamber, it was immediately pumped down to remove the air introduced during the loading of the chamber. If the contents of the chamber contained no sealed containers, the chamber was fully pumped down. If, on the other hand, there were closed containers (as is the case when bringing silane reagent bottles into the box) then the chamber was not pumped down completely and instead of 3 pump cycles there are 4 to 5. This was to prevent the bottles from breaking from the pressure differential. Once everything was in the box, the solution was made in a volumetric flask and then subsequently added to the staining dish containing the slides. The cover was put on the dish and the contents allowed to stir for 1 hour in the dry box. After the hour was complete, the dish was removed from the dry box and placed in the fumehood and stirred for an additional 15 minutes. The stirring was then stopped and each slide was removed and rinsed with ethanol into a waste jar and then dipped into a beaker containing DI water. The slide was swirled around and the cycle repeated. After the final ethanol wash the slides were placed into a clean staining dish without drying with $N_2$. Once all the slides had been cleaned and placed in the dish, the entire dish (plus lid) was placed in the drying oven (at 100° C.) for 30 minutes. After the 30 minutes the lid was placed on the dish and removed from the oven and placed on the counter to cool.

Aqueous Procedure

Polyarginine stock solution was prepared as follows:
21 mL 0.1% polyarginine solution (w/v in distilled water)
21 mL 1×PBS buffer
168 mL distilled water
1. Clean microscope slides were immersed in polyarginine solution for 1 hour with stirring.
2. Slides were removed from the polyarginine solution and plunged up and down 5 times in distilled water to rinse.
3. Slides were spun dry for 2 minutes at 1000 rpm using a vacuum spinner.
4. Slides were dried at 45° C. for 10 minutes.

Instrumentation
1. The DNA was printed using the Cartesian Technologies printer and the associated software package. A quill pin was used to print the arrays. Before each group of slides were printed the pin was sonicated in arrayit micro cleaning solution for 5 minutes followed by isopropanol for 5 minutes.
2. The arrays were visualized using the General Scanner ScanArray 3000 system. This system has the lasers (2) tuned for Cye 3 and Cye 5 fluorescent dyes.

DNA Printing
1. The microscope slide was printed with a 10×10 array of spots using the 1.5 Kb double stranded DNA PCR product (pBR322; pst I to sal I vector) at 100 nmol/uL (~100 ng/uL).
2. The slides were scanned using the ScanArray 3000.
3. The slides were then incubated at 100° C. for 4 hours (or can be vacuum dried in a bell jar dessicator for 3 days). The drier the slides are the better they will hybridize and the better the retention will be.

Prehybridization
1. The slides were then pre-hybridized for 45 minutes in a Copeland jar containing a solution containing 25% formamide, 5×SSC, 0.1% SDS that has been warmed to 42° C. If necessary, 1% BSA can be added for blocking.
2. The slides were rinsed under distilled water and IPA and then dried with nitrogen.

Denaturation
1. Slides were placed in boiling water for two minutes.
2. Slides were rinsed with IPA and dried with nitrogen.
3. Slides were rescanned.

Hybridization
1. Probe DNA was 0.01 pmol/uL in hybridization buffer.
2. The probe (20 uL) were added to the slide and slowly the cover slip added.
3. The slide was put into hybridization chamber (Corning hyb chamber) with 20 uL water for humidity.
4. The hybridization chamber was sealed and put in water bath at 42° C. overnight.

Washing
1. The slide with cover slip was placed in large volume 2×SSC/0.1% SDS (2×SSC/0.01% IS AT 42° C.).
2. The cover slip was allowed to come off.
3. The slide was rinsed with 2×SSC/0.01% SDS (5 min. 42° C.) in a Copeland jar.
4. The slides was rinsed with 0.1×SSC/0.1% SDS at room temp (10 min.) in a Copeland jar.
5. The slide was rinsed with 0.1×SSC (1 minute; 4 repeats) in a Copeland jar.
6. The slide was rinsed with running water less than 10 seconds.
7. The slide was rinsed with ETOH and dried with nitrogen.
8. The slide was scanned with ScanArray 3000 (both the Cy3 and Cy5 channel).

Results

Figure 1B:
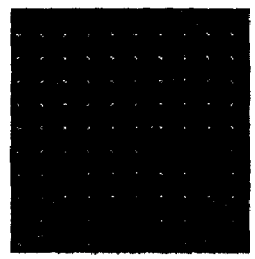
Figure 1C:
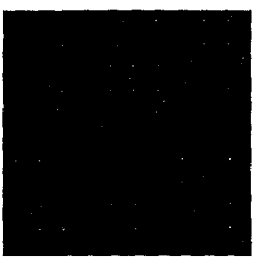
Figure 1D:
Figure 1E:
Figure 1F:
Figure 1G:
Figure 1H:
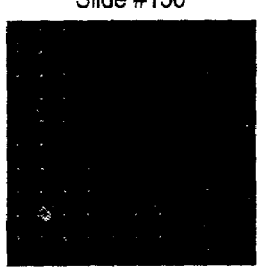

FIG. 1 shows data from 2 slides (149 and 150) coated with [4-[2-(trichlorosilyl)ethyl]pyridine (United Chemical)] (referred to as "pyridinium"), the slides that were printed, prehyb/boil, and hybridized as discussed above. The numbers in parenthesis are the laser power: PMT setting (i.e. 65:65). The lower the numbers the more material is there. The false color images are a measure of the intensity with blue being the lowest and white being the highest values. The two hyb channels are indicative of the two dyes used. Channel 1 is Cy3 and channel 2 is Cy5. Channel 1 was used to detect hyb signal and channel 2 was used to monitor print signal. Looking at the prehyb/boil signal one can see that the spots were very uniform without smearing or merging. The hyb signals were a little weak but this surface was not optimized.

Figure 2C:
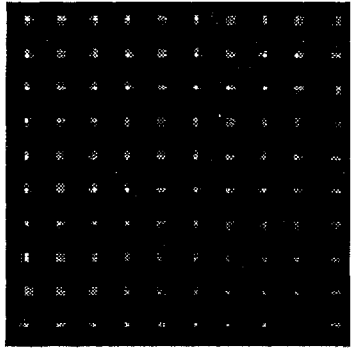
FIGS. 2A–2L show false color images from three slides coated with polyarginine.
Figure 2F:
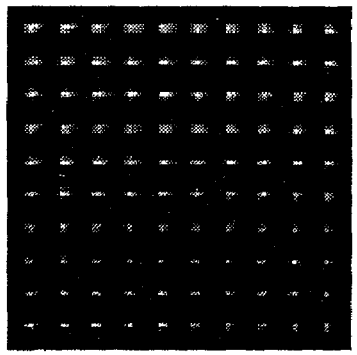
Figure 2B:
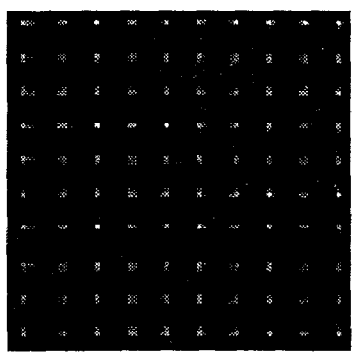
Figure 2E:
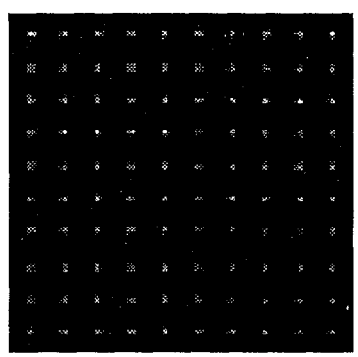
Figure 2A:
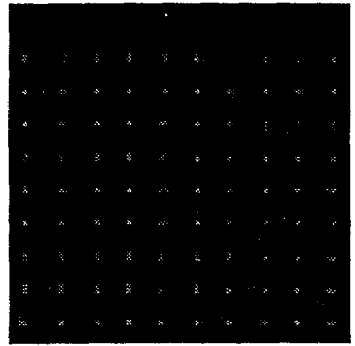
Figure 2D:
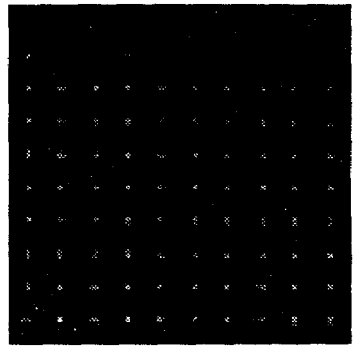
Figure 2G:
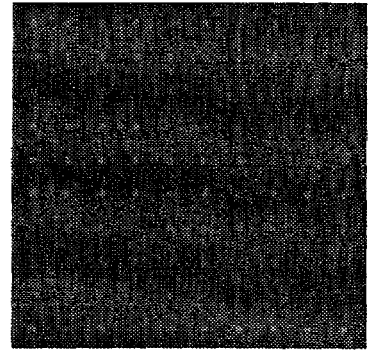
Figure 2J:
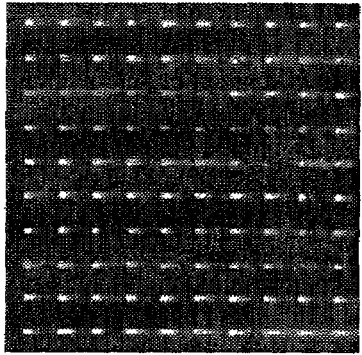
Figure 2H:
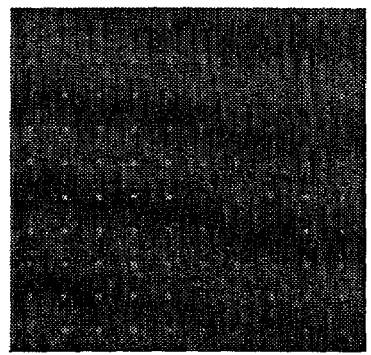
Figure 2K:
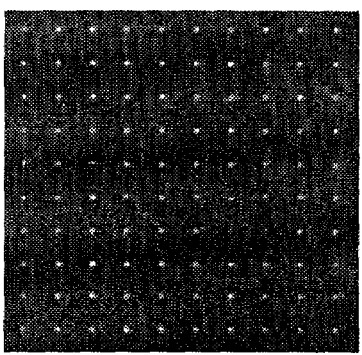
Figure 2I:
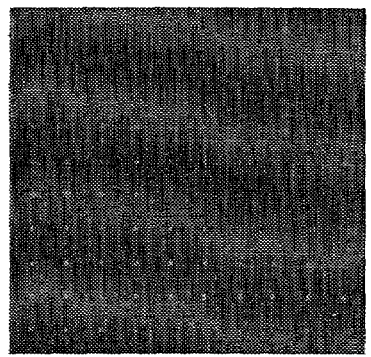
Figure 2L:
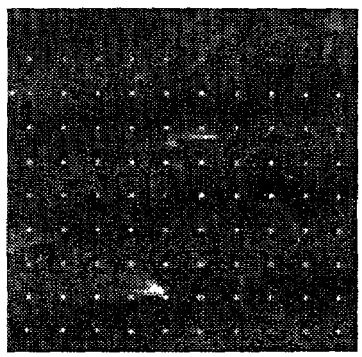

FIG. 2 shows the data from 3 different slides coated with poly-L-arginine hydrocholoride (mw 5,000–15,000 (Aldrich)) referred to as "polyarginine." The slides were treated as discussed above. Slide #387 was ~1 month old and slides #482, 483 were freshly made. The prehyb/boil signal for #387 and 482 was very nice with strong signal (65:65). Slide #483 illustrates the effect of BSA as a blocking agent with the spots smearing during the prehyb/boil step. The hyb signal for all slides was strong (85:85).

Figure 3A:
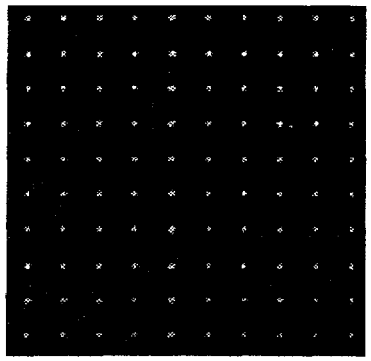
Figure 3B:
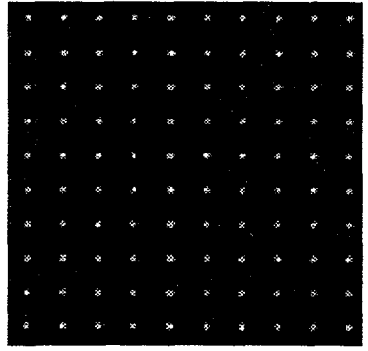
Figure 3C:
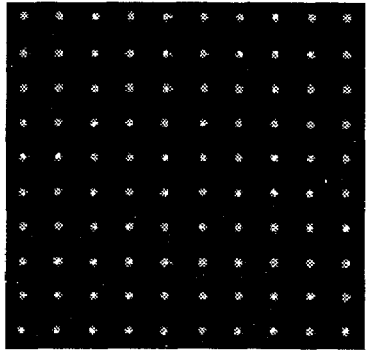
Figure 3D:
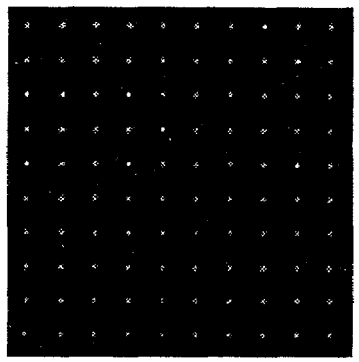
Figure 3E:
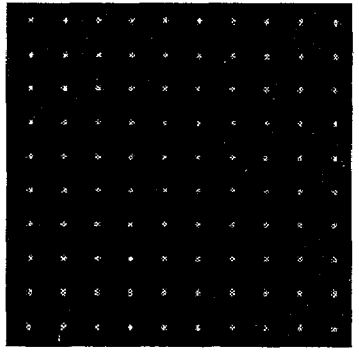
Figure 3F:
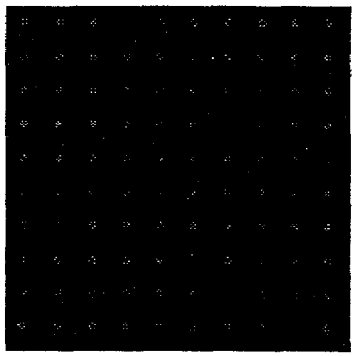

N-(trimethoxysilylpopyl) isothiouronium chloride (Gelest) (referred to as "thiouronium") was used to coat a clean microscope slide as discussed above. The slides were treated as discussed above. As shown in FIG. 3, old slide #320 (~55 days) did not fair as well as the new slide with BSA #472. Again, the effect of BSA was pretty dramatic as seen in slide #473.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A reagent composition for attaching a target molecule to the surface of a substrate comprising functional groups of the general formula (I):

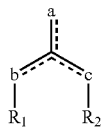

wherein
- - - - - represents a single or double bond forming a saturated or unsaturated portion of said functional group, provided that only one is unsaturated at a given time;
a is N or H;
b is S, N, C or O;
c is N; and
$R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other; and
further wherein c is protonated at acidic pH.

2. The reagent composition of claim 1, wherein said functional group of general formula (I) has an atom with a cationic charge conjugated to an atom with a lone pair of electrons.

3. The reagent composition of claim 2, wherein said functional group of general formula (I) is a guanidine or thiouronium group.

4. The reagent composition of claim 3, wherein said functional group of general formula (I) is selected from the group:

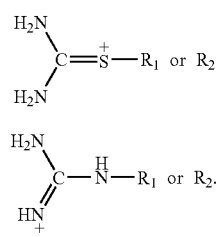

5. The reagent composition of claim 1, wherein the target molecule interacts with said functional group by hydrogen bonding and ionic interactions.

6. The reagent composition of claim 5, wherein a phosphate group on the target molecule interacts with said functional group by hydrogen bonding and ionic interactions.

7. A method for attaching target molecules on the surface of a substrate comprising the steps:
a) providing upon the surface of a substrate a reagent composition comprising functional groups of the general formula (I):

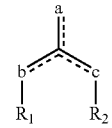

wherein
- - - - - represents a single or double bond forming a saturated or unsaturated portion of said functional group, provided that only one is unsaturated at a given time;
a is N or H;
b is S, N, C or O;
c is N; and
$R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other;
further wherein c is protonated at acidic PH;
b) providing a solution comprising a target molecule;
c) applying one or more spots of the same solution on the surface of the substrate surface; and
d) allowing the functional group to interact with the target molecule.

8. The method of claim 7, wherein the functional group of general formula (I) has an atom with a cationic charge and an atom with a lone pair conjugated to each other.

9. The method of claim 8, wherein the functional group of the general formula (I) is a guanidine or thiouronium group.

10. The method of claim 9, wherein said functional group of general formula (I) is selected from the group:

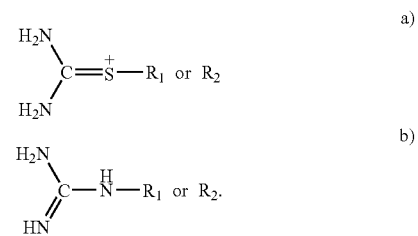

11. The method of claim 7, wherein the target molecule is DNA or RNA.

12. The method of claim 11, wherein the DNA is an oligonucleotide.

13. The method of claim 7, wherein the target molecule interacts with said functional group by hydrogen bonding and ionic interactions.

14. The method of claim 7, wherein the substrate comprises a material selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin and polyacetates.

15. A substrate coated with a reagent composition comprising functional groups of the general formula (I):

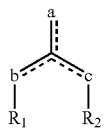

wherein
.....represents a single or double bond forming a saturated or unsaturated portion of said functional group, provided that only one is unsaturated at a given time;
a is N or H;
b is S, N, C or O;
c is N; and
$R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other;
further wherein c is protonated at acidic pH.

16. The substrate of claim 15, wherein the functional group of general formula (I) has an atom with a cationic charge and an atom with a lone pair conjugated to each other.

17. The substrate of claim 15, wherein the functional group of the general formula (I) is a guanidine or thiouronium group.

18. The substrate of claim 15, wherein said functional group of general formula (I) is selected from the group:

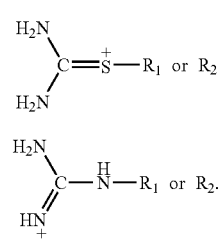

19. The substrate of claim 15, further comprising a target molecule.

20. The substrate of 19, wherein the target molecule is a DNA or RNA.

21. The substrate of claim 20, wherein the DNA is an oligonucleotide.

22. The substrate of claim 15, wherein the substrate comprises a material selected from the group consisting of silica, silicon, germanium, gallium, arsenide, epoxy resin, polystyrene, polysulfone, aluminum, platinum, alumina, silicone, fluoropolymers, polyesters, acrylic copolymers, polyglactin and polyacetates.

23. A reagent composition for attaching a target molecule to the surface of a substrate comprising functional groups of the general formula (I):

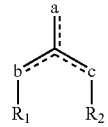

wherein
.....represents a single or double bond forming a saturated or unsaturated portion of said functional group, provided that only one is unsaturated at a given time;
a is N or H;
b is S, N, C or O;
c is N; and
$R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other or part of a conjugated ring system, wherein the functional group is not pyridyl; and
further wherein c is protonated at acidic pH.

24. A reagent composition for attaching a target molecule to the surface of a substrate comprising functional groups of the general formula (I):

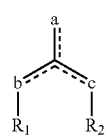

wherein
.....represents a single or double bond forming a saturated or unsaturated portion of said functional group, provided that only one is unsaturated at a given time;
a is N or H;
b is S, N, C or O;
c is N; and
$R_1$ and $R_2$ are each independently selected from a hydrogen, alkyl, alkynyl, alkenyl, aryl, araalkyl, heteroalkyl, heteroalkynyl, heteroalkenyl, heteroaryl, heteroaraalkyl group and are independent of each other or part of a conjugated ring system; and
further wherein c is protonated at acidic pH,
wherein the target molecule interacts with the functional group by hydrogen bonding and ionic interactions.

25. A substrate coated with the reagent composition of claim 23.

26. A substrate coated with the reagent composition of claim 24.

* * * * *